United States Patent [19]
Axelrod

[11] 3,979,452
[45] Sept. 7, 1976

[54] THIOFORMAMIDE IMPROVED PROCESS
[75] Inventor: Eugene H. Axelrod, Old Bridge, N.J.
[73] Assignee: Merck & Co., Inc., Rahway, N.J.
[22] Filed: Sept. 23, 1974
[21] Appl. No.: 508,789

Related U.S. Application Data

[63] Continuation of Ser. No. 384,544, Aug. 10, 1973, abandoned, which is a continuation-in-part of Ser. No. 210,222, Dec. 20, 1971, abandoned.

[52] U.S. Cl. ............................................. 260/551 S
[51] Int. Cl.$^2$ ..................................... C07C 153/057
[58] Field of Search ................................ 260/551 S

[56]      References Cited
       UNITED STATES PATENTS 3,274,243   9/1966   Gilbert et al. ..................... 260/551
3,336,381   8/1967   Gilbert et al. ..................... 260/551 S
3,346,632   10/1967  Tull et al. ......................... 260/551 S

OTHER PUBLICATIONS

Helfferich, Ion Exchange, pp. 47–58 (1962).

Primary Examiner—Daniel E. Wyman
Assistant Examiner—Thomas A. Waltz
Attorney, Agent, or Firm—David L. Rose; J. Jerome Behan

[57]              ABSTRACT

Thioformamide is prepared from hydrogen cyanide and hydrogen sulfide in an improved process employing a tertiary amino ion exchange resin as the catalyst. The process provides for nearly quantitative yields, and affords a purer, more stable product, and the elimination of polluting by-products.

6 Claims, No Drawings

THIOFORMAMIDE IMPROVED PROCESS

CROSS REFERENCE TO RELATED APPLICATIONS

This application is a continuation of U.S. Ser. No. 384,544 filed August 1, 1973, now abandoned, which is a continuation-in-part of U.S. Ser. No. 210,222, filed December 20, 1971, now abandoned.

This invention relates to an improved process for the preparation of thioformamide from hydrogen cyanide and hydrogen sulfide with an insoluble basic catalyst. One object of the invention is thus to provide a process whereby thioformamide is prepared in nearly quantitative yields without the concomitant preparation of by-products. A further object is to prepare thioformamide free of residual soluble catalysts by employing an insoluble tertiary amine ion exchange resin. A still further object is to provide a process which affords no polluting waste materials. Another object is to provide a process which is adaptable to either batch or continuous use. Further objects will become apparent on a further reading of the disclosure.

DESCRIPTION OF THE PRIOR ART

Thioformamide has traditionally been prepared by the action of phosphorous pentasulfide on formamide, a process which is, however, a difficult one and one which involves costly starting materials. Another method involves the reaction of hydrogen sulfide with hydrogen cyanide in the presence of a soluble basic catalyst. This process is described in U.S. Pat. No. 3,346,632. The instant process is an improvement over this method offering many advantages over it.

DESCRIPTION OF THE INVENTION

The process of this invention employs an insoluble tertiary amine ion exchange resin as a catalyst for the conversion of hydrogen cyanide and hydrogen sulfide into thioformamide. The ion exchange resin is insoluble in the reaction solvent. Any organic solvent may be employed in this process. Suitable solvents include loweralkanols such as methanol, ethanol, propanol, isopropanol, 1-butanol, and the like; glycols, such as ethylene glycol, propylene glycol, and the like; ethers such as ethyl ether, tetrahydrofuran, and the like; aromatic hydrocarbons such as naphthalene, benzene, toluene, xylene, and the like; aliphatic hydrocarbons such as pentane, hexane, heptane, and the like; esters such as methyl formate, ethyl formate, amyl acetate, methyl propionate, and the like; halogenides, such as chloroform, dichloroethane, and the like; dimethylsulfone, dimethylformamide, dimethylsulfoxide, and similar solvents, or mixtures thereof.

The non-reactive portion of the ion exchange resin, often termed the "backbone" of the resin, may be any polymer insoluble in the solvents employed. Suitable backbone structures are synthetic polymers based on polystyrene, polyacrylamide and the like and natural polymers such as cellulose. Of the many types of anion exchange resins currently available, examples of those suitable for use in the instant invention are Amberlite IRA-93, and IRA-94, trade names for an anion exchange resin with a styrenedivinyl-benzene polymer backbone and tertiary amine basic groups marketed by Rohm and Haas Company and IRA-68, a trade name for an anion exchange resin with polyacrylamide backbone and tertiary amine basic groups, also marketed by Rohm and Haas. Other tertiary amine anion exchange resins may be also employed with satisfactory results.

It has been discovered that when ion exchange resins other than tertiary amine resins are employed, the yields of thioformamide are substantially reduced affording less than 1% of product and accompanied by a substantial quantity of polymeric by product in the form of an intractable mass. Thus for the preferred operation of the instant process, ion exchange resins achieving their basicity from tertiary amine functions should be employed. The use of tertiary amine resins avoids such intractable polymeric by-products and affords only thioformamide in nearly quantitative yields.

The reaction is preferably run at a temperature of from −40° to 100°C. with from 0 to 60°C. being most preferred. The duration of the reaction is from 1 to 100 hours with most reactions being completed in from 3 to 75 hours. The reaction may be alternatively carried out at atmospheric pressure or under a positive pressure. It may be somewhat mechanically facilitated by employing positive pressure reaction conditions as two gaseous reactants are being reacted with each other, and a positive pressure would tend to keep the reagents in solution.

The amount of the ion exchange resin necessary to properly catalyze the reagents is from 2 to 40 mole percent the preferably from 7 to 15 mole percent. The mole percent of the catalyst is determined by the total number of basic functions on the polymeric backbone. One mole of each of the reagents thus requires from 0.02 to 0.4 moles of basic functions on the ion exchange resin. If less than about 2 molar percent is employed, the reaction will take an impractically long period of time to go to completion.

In order to maximize the yields and form a minimum of by-products the reaction is preferably stopped when from 20 to 50%, most preferably about 30%, of the starting materials have been consumed. The reaction is allowed to proceed to this point whereupon the solution containing the unconsumed starting materials and the desired product is separated from the catalyst. The gaseous starting materials can be removed from the solution and reused in subsequent reactions. The starting materials are most easily removed from the reaction mixture by heating the solution, placing it under a partial vacuum or a combination thereof. By stopping the reaction when it is only partially complete, lower concentrations of the product are maintained, thus affording less opportunity for the product to decompose or react with starting materials, forming unwanted by-products. The extent of the reaction may be monitored by spectrographic techniques such as infrared or ultraviolet spectra or the analysis of an aliquot portion to determine the degree of completion of the reaction.

In one aspect of this process the reaction is performed by combining the reagents in the desired solvent in approximately equimolecular portions with tertiary amine anion exchange resin and agitating the reaction mixture until the optimum amount of the reagents have been consumed. While an excess of one of the gaseous reagents may be employed over the other, no advantage has been observed thereby, and approximately equimolecular portions facilitates the recycling of the excess combined gases. Since the anion exchange resin is insoluble in the solvents employed in this process, the reaction mixture is preferably agitated during the reaction period to insure proper contact between the reagents in solution and suspened resin.

When the process has reached the desired degree of completion it is filtered, affording a solution containing only thioformamide and unreacted starting materials. The starting materials are removed using heat and/or vacuum affording a solution of thioformamide in which the yield is quantitative or nearly quantitative based upon the starting materials actually consumed. The solution of thioformamide after removing the starting materials is stable for extended periods of time at room temperature. This stability is an improvement over prior processes. The prior art processes afford a solution of thioformamide which contains a quantity of soluble basic catalyst. The presence of the catalyst tends to decompose the product and polymerize the hydrogen cyanide when purification techniques, such as heating, are attempted. In addition, room temperature storage of thioformamide as a solution or a meltable solid with minute quantities of basic catalyst therein also tends to decompose the compound. By removing all of the resin from the solution by filtration this problem is avoided and pure stable solutions of thioformamide are obtained, which can be purified without danger of decomposing the thioformamide.

In addition, the elimination of by-products, particularly the hydrogen cyanide polymer, obviates serious disposal problems. Everything in this process is recyclable. The resin is generally reusable, excess starting materials can be recycled, and the solvent, when the product is removed therefrom, can be purified and reused. Thus serious problems of pollution with industrial waste are avoided with this process.

In a further aspect of this invention, the process described above is adapted for continuous operation. In one embodiment of the continuous process the anion exchange resin is contained in a vessel and a solution or solutions of the starting materials continuously added to and removed therefrom.

A preferred embodiment of this aspect is the utilization of a stationary column of the anion exchange resin in which a solution of the reagents passes therethrough. The rate of passage and the length of the column would determine the degree of completion of the reaction and these factors could be adjusted using techniques known to those skilled in this art such that about 30% of the starting materials are consumed, affording maximum yields.

In order that this invention may be more fully understood, the following examples are presented. The examples are exemplary of the various embodiments of the invention are not restrictions thereof.

EXAMPLE 1

2.86 G. of hydrogen cyanide and 5 g. (about 8–10 moles percent) of Amberlite IRA-94 ion exchange resin is added to 50 ml. of isopropyl alcohol and the mixture is shaken at 50 psig. pressure of hydrogen sulfide for 17.5 hours at 25°C. The excess hydrogen sulfide is vented and the reaction mixture filtered. The remaining hydrogen cyanide is removed by distilling the filtered mixture. The recovered hydrogen cyanide amounts to 1.98 g. and the distillation residue contains 1.96 g. of thioformamide (98% yield based on the hydrogen cyanide actually converted) as a solution in isopropyl alcohol. The thioformamide contained in the solution is isolated by distilling off the bulk of the alcohol at reduced pressure, and crystallizing the residue from ethyl acetate at −78°. The thioformamide has a m.p. of 33°C.

EXAMPLE 2

The quantities of reagents of Example 1 are combined with 5 g. of Amberlite IRA-68 resin and heated at 60°C. under 250 psig. When the ultraviolet absorption of an aliquot indicates that about 21% of the reagents have been consumed (about 1 hour) the reaction is stopped and worked up as in Example 1. The yield is 96% of thioformamide of the converted starting materials.

EXAMPLE 3

The same quantities of reagents as are employed in Example 1 are combined with 5 g. of Amberlite IRA-93 resin and stirred at 20°C. for 16 hours at about 2 psig. The reaction mixture is worked up as in Example 1 affording 95% yield of thioformamide at 38% conversion of the starting materials.

EXAMPLE 4

A vertical column 12 inches high by 2 inches in diameter is packed with Amberlite IRA-94 resin and isopropyl alcohol. The column is heated to 40°C. and pressurized with hydrogen sulfide at 50 psig. A solution of hydrogen cyanide in isopropanol at a concentration of 27 g. of hydrogen cyanide per 500 ml. is passed slowly through the column maintaining the pressure at 50 psig. The rate of flow is such that the effluent contains 3.6 g. of thio-observing the ultraviolet absorption of the effluent at 265 nanometers. The effluent is passed continuously into a distillation apparatus. The unconsumed hydrogen cyanide and hydrogen sulfide along with a portion of the isopropanol are collected by distillation. The residue contains pure thioformamide and isopropanol. The distillate is returned to the resin column, supplementing it with hydrogen cyanide are repressurizing it with hydrogen sulfide such that the original concentrations are obtained. The isopropanol is distilled from the residue affording pure thioformamide, m.p. 33°C. recovered in 97% yield based on the starting materials actually consumed.

What is claimed is:

1. An improved process for the preparation of thioformamide wherein hydrogen cyanide and hydrogen sulfide are combined in the presence of a basic catalyst, the improvement comprising employing an insoluble tertiary amine anion exchange resin in an organic solvent at from −40° to 100°C. as a catalyst for the reaction.

2. The process of claim 1 wherein the starting materials are reacted at from −40° to 100°C. at a pressure greater than or equal to atmospheric pressure.

3. The process of claim 1 wherein the reaction is stopped when from 20 to 50% of each of the starting materials is consumed.

4. The process of claim 1 wherein the reaction is a continuous process.

5. The process of claim 4 wherein the starting materials are continuously passed over a stationary column of the ion exchange resin.

6. An improved process for the preparation of thioformamide wherein hydrogen cyanide and hydrogen sulfide are combined in the presence of a basic catalyst, the improvement comprising employing an insoluble tertiary amine anion exchange resin in an organic solvent at a reaction temperature of from −40° to 100°C. at a pressure greater than or equal to atmospheric pressure and wherein the thioformamide is isolated when from 20 to 50% of each of the starting materials is consumed.

* * * * *